United States Patent [19]

Zimmermann

[11] Patent Number: 5,364,521
[45] Date of Patent: Nov. 15, 1994

[54] APPARATUS FOR PERFORMING CAPILLARY ELECTROPHORESIS

[75] Inventor: Hans-Peter Zimmermann, Karlsbad, Germany

[73] Assignee: Hewlett-Packard Company, Palo Alto, Calif.

[21] Appl. No.: 83,731

[22] Filed: Jul. 1, 1993

[30] Foreign Application Priority Data

Aug. 4, 1992 [EP] European Pat. Off. ......... 92113244.5

[51] Int. Cl.⁵ ............................................. B01D 61/42
[52] U.S. Cl. ................................................ 204/299 R
[58] Field of Search ......................... 204/299 R, 180.1

[56] References Cited

U.S. PATENT DOCUMENTS

| | | | |
|---|---|---|---|
| 4,242,909 | 1/1981 | Gundelfinger | 73/422 GC |
| 4,713,974 | 12/1987 | Stone | 73/864.23 |
| 5,019,236 | 5/1991 | Young | 204/180.1 |

FOREIGN PATENT DOCUMENTS

| | | |
|---|---|---|
| 0838459A2 | 8/1990 | European Pat. Off. . |
| 0448313A2 | 9/1991 | European Pat. Off. . |
| 0475533A2 | 3/1992 | European Pat. Off. . |
| 2057288A | 1/1981 | United Kingdom . |

OTHER PUBLICATIONS

Characterization and Automation of Sample Introduction Methods for Capillary Zone Electrophoresis: Donald J. Rose, Jr., and James W. Jorgenson; Apr. 1, 1988; pp. 1-7.

*Primary Examiner*—John Niebling
*Assistant Examiner*—Edna Wong

[57] ABSTRACT

An apparatus for performing capillary electrophoresis comprises a housing (37) to which a sealing and electrode arrangement (36) is fastened and a removable cassette (22) which accommodates a capillary (1) in which electrophoretic separation of a sample takes place when an electric field is applied. When performing an electrophoretic separation, the end of the capillary (1) and a tube-shaped electrode (39) surrounding the capillary (1) dip into a liquid vial containing electrolyte or sample liquid. Liquid is injected into the capillary (1) by applying pressure on the liquid in the vial. An elastomeric seal (40) around the capillary (1) is provided to prevent escaping of the pressure during injection. The end of the capillary (1) depending from the cassette (20) is introduced through a funnel (41) and a central bore in the seal (40). When the cassette (20) is pressed downwards onto the funnel (41), the elastomeric seal (40) is squeezed so that the capillary (1) is sealed off. Since the seal (40) is arranged in the housing (37), no sealing is required in the cassette, resulting in a simpler construction of the cassette and facilitating replacement of the capillary in the cassette. (FIG. 4)

12 Claims, 6 Drawing Sheets

APPARATUS FOR PERFORMING CAPILLARY ELECTROPHORESIS

The invention relates to an apparatus for performing capillary electrophoresis.

BACKGROUND OF THE INVENTION

Capillary electrophoresis is a separation method employed in analytical chemistry which utilizes the differences in electrophoretic mobility of the sample substances to be separated. Capillary electrophoresis is used, for example, for separating different biological molecules, such as proteins or peptides. The separation process is performed in a capillary tube which is open on both ends and to which an electric field is applied which causes electrophoretic separation of different sample substances within the tube. The electric field is applied by means of electrodes which are arranged at the ends of the capillary, respectively, and which are connected to a high voltage power supply. The capillary is filled with an electrically conductive electrolyte so that an electric field can build up within the capillary. The two ends of the capillary are immersed in vials containing the electrolyte, respectively.

When sample substances are to be introduced into the capillary for subsequent separation, the vial containing the electrolyte is removed from one end of the capillary, a vial containing the sample is positioned at this place so that the end of the capillary is immersed in the sample liquid. Thereafter, the sample is injected into the capillary by a suitable method, for example by applying a pressure above atmospheric pressure at the end of the capillary where the vial is positioned or a vacuum at the other end of the capillary. When the sample substances have been injected into the capillary, the sample vial is removed and the electrolyte vial is again positioned at this place. Thereafter, high voltage is applied so that electrophoretic separation of the sample substances takes place. At the end of the capillary opposite to the end of sample injection, a detector is arranged for detecting the separated sample substances by a suitable detection method, for example by a light absorption or a fluorescence technique.

A frequently used method for introducing liquids, such as electrolyte, sample liquid and rinsing liquids into the capillary, is to apply a pressure difference between the two ends of the capillary. This pressure difference forces liquid into the capillary. When applying this method, the capillary has to be sealed against the vial in which the liquid to be introduced is contained to prevent escaping of the pressure to the outside.

In the prior art, there are different solutions for designing the mentioned seal between capillary and vial. According to a first solution, liquid is introduced into the capillary by applying a pressure below atmospheric pressure at the outlet end of the capillary where the detector is located. In this case, the electrolyte, vial at the outlet end of the capillary is connected with the capillary by a screw fastening. The screw fastening also performs the sealing function. This design has the disadvantage that it is not possible to exchange the electrolyte vial at the outlet end of the capillary during an analysis sequence since the end of the capillary and the vial are rigidly connected. Furthermore, since the introduction of liquid is performed by application of underpressure, there is only a maximum pressure difference of 1 bar available. In practice, the usable pressure difference would only be about half of this value because the gas emissions from the liquids would otherwise be too strong.

In a second design solution for the sealing of the capillary against a vial, the capillary is disposed in a cartridge body and the two ends of the capillary protrude vertically downward from the bottom of the cartridge, at two spaced apart locations at the bottom of the cartridge. These two ends are sealed about their periphery with respect to the cartridge where they exit the cartridge. For introducing liquid into the capillary, the corresponding vial is pressed against the bottom of the cartridge, then an over-pressure is applied on the liquid in the vial, forcing the liquid into the capillary. A capillary electrophoresis apparatus using this design is known from EP-A-0 339 780.

With such a known design, a sealing of the periphery of the capillary to the cartridge is achieved by injecting a sealant, preferably a silicon rubber compound, into apertures near the bottom of the cartridge. A design of that type is not satisfactory in all respects. When the capillary in the cartridge is to be replaced, for example when the capillary is broken, a user has to remove the sealant, and then, after insertion of a new capillary, he has to renew the sealing by filling in sealant into the corresponding apertures in the cartridge. This is a time-consuming process and requires that the user has the sealing material (e.g., silicon rubber) at his disposal. On the other hand, if the user wants to avoid this time-consuming process and just takes a new cartridge with a sealed capillary inside, this becomes more expensive since he also has to bear the cost for the cartridge, whereby the cost is still increased by the sealing.

SUMMARY OF THE INVENTION

It is thus an object of the present invention to provide an apparatus for performing capillary electrophoresis wherein the capillary is arranged in a removable cassette which ensures a simpler and faster replacement of the capillary.

It is a further object of the invention to provide an apparatus for performing capillary electrophoresis having a simple and reliable sealing of the capillary.

According to the present invention, these objects are solved by an apparatus as defined in claim 1. According to claim 1, the capillary electrophoresis apparatus of the invention comprises a cassette for receiving the capillary, with the inlet end and the outlet end of the capillary projecting from the cassette; it further comprises a housing into which the cassette can be inserted for performing electrophoresis, and a sealing arrangement associated with the housing, with the sealing arrangement forming a seal around an end of the capillary when the cassette is inserted in the housing.

It is an underlying principle of the invention that the seal for sealing the capillary against escaping of pressure is associated with the housing of the electrophoresis apparatus, in contrast to the prior art wherein the seal is arranged in the capillary cassette. Consequently, the invention permits fast and easy replacement of the capillary in the cassette; no seals have to be removed in order to remove the capillary from the cassette. The invention thus also provides for a cost-saving cassette.

In a preferred embodiment of the invention, the seal is made of an elastomeric material which is deformed when the cassette is inserted into the electrophoresis apparatus. Thus, the elastomeric material is pressed against the outside of the capillary, providing for a hermetic seal.

The sealing arrangement in an embodiment of the invention, the sealing arrangement may comprise a funnel-shaped part which captures the end of the capillary when the cassette is introduced into the electrophoresis apparatus. This funnel-shaped part can be resiliently mounted to the rest of the sealing arrangement so that it is pressed against the elastomeric seal by the bottom of the cassette when the cassette is pushed into the electrophoresis apparatus.

In a further embodiment of the invention, the electrode for applying high voltage is a conductive tube connected to the sealing arrangement through which the capillary is pushed when the cassette is inserted. In that way, both the sealing of the capillary and the application of high voltage are realized with a space saving and mechanically simple construction. Furthermore, the electrode tube fulfills the additional task of protecting the capillary.

The cassette for accommodating the capillary may comprise a detector interface which is essentially a housing through which the outlet end of the capillary is guided and held in very precise geometrical relationship to the housing. The detector interface is mounted to the cassette such that it remains movable within a small range relative to the cassette. With this floating mounting of the cassette interface, engagement with the corresponding counterpart in the detector is facilitated when the cassette is pushed into the apparatus.

According to an embodiment of the invention, the electrophoresis apparatus comprises a swivelling cassette adapter into which the cassette is inserted. When inserting the cassette, the operator tilts the adapter away from its normal upright position; when the cassette is completely inserted, the adapter returns to the upright position. The advantage of the swivelling arrangement is that it is avoided that the projecting detector interface is blocked by the mating part of the detector in the electrophoresis apparatus during insertion of the cassette.

BRIEF DESCRIPTION OF THE DRAWINGS

Subsequently, an embodiment of the invention is explained in detail with reference to the drawings.

DETAILED DESCRIPTION OF THE INVENTION

Figure 1:
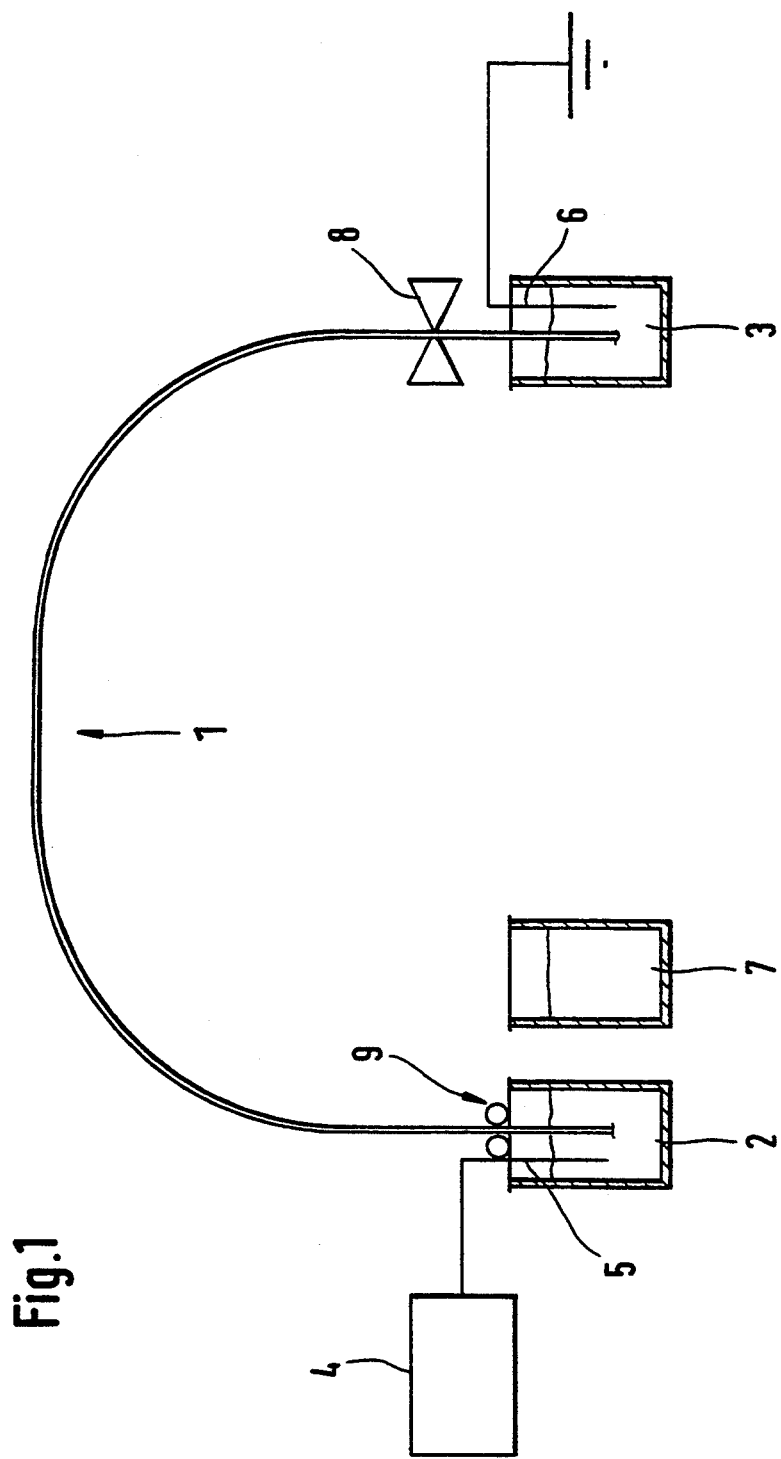
FIG. 1 is a schematic diagram illustrating the basic components of a capillary electrophoresis apparatus.

FIG. 1 schematically depicts the components of a capillary electrophoresis apparatus. The separation capillary 1 is immersed with its inlet end in a first vial 2 containing electrolyte and with its outlet end in a second vial 3 which also contains electrolyte. An electric field is applied along the capillary 1 by a high-voltage power supply 4 via an electrode 5 at the inlet end of the capillary 1. An electrode 6 at the outlet end of the capillary 1 is connected to ground potential. A sample vial 7 contains the sample substances to be separated electrophoretically. For introducing the sample substances into the capillary 1, the vial 2 is replaced by the sample vial 7 and a plug of sample liquid is injected into the capillary 1 by suitable injection means (not shown). The sample substances separated in the capillary 1 are detected by a detector 8 which is arranged at the outlet end of the capillary 1. The detector 8 can be, for example, a UV absorbance detector. The detector 8 is connected to a processing circuit (not shown) which produces signals indicative of the substances passing the detector. The capillary 1 is typically made of fused silica.

Liquid is introduced into the capillary 1 by applying a pressure difference between the vial 3 at the outlet end of the apparatus and the vial 2 (or 7) at the inlet end of the capillary 1, in a preferred embodiment of the invention, a pressure above atmospheric pressure is applied on the liquid in the vial 2 (or 7) at the inlet end and the via) 3 at the outlet end is kept at atmospheric pressure. In order to ensure that the applied pressure cannot escape, a sealing arrangement 9 around the capillary 1 is required. The geometrical arrangement of the seal 9 within the electrophoresis apparatus and in relationship to the electrode 5 as well as the design of the seal are important aspects of the present invention. The corresponding details will be described below.

Figure 2:
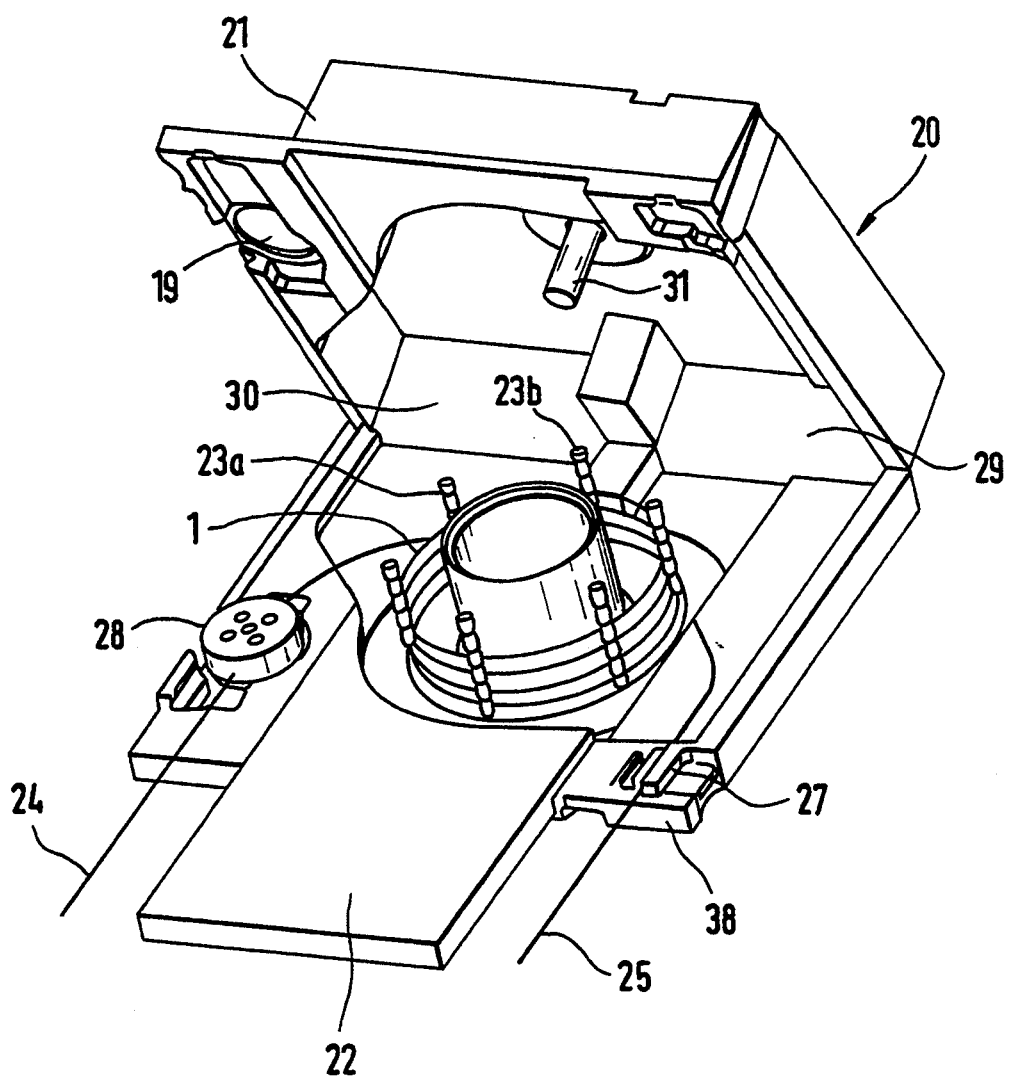
FIG. 2 shows a capillary cassette which can be inserted into a capillary electrophoresis apparatus in accordance with the invention.
Figure 3:
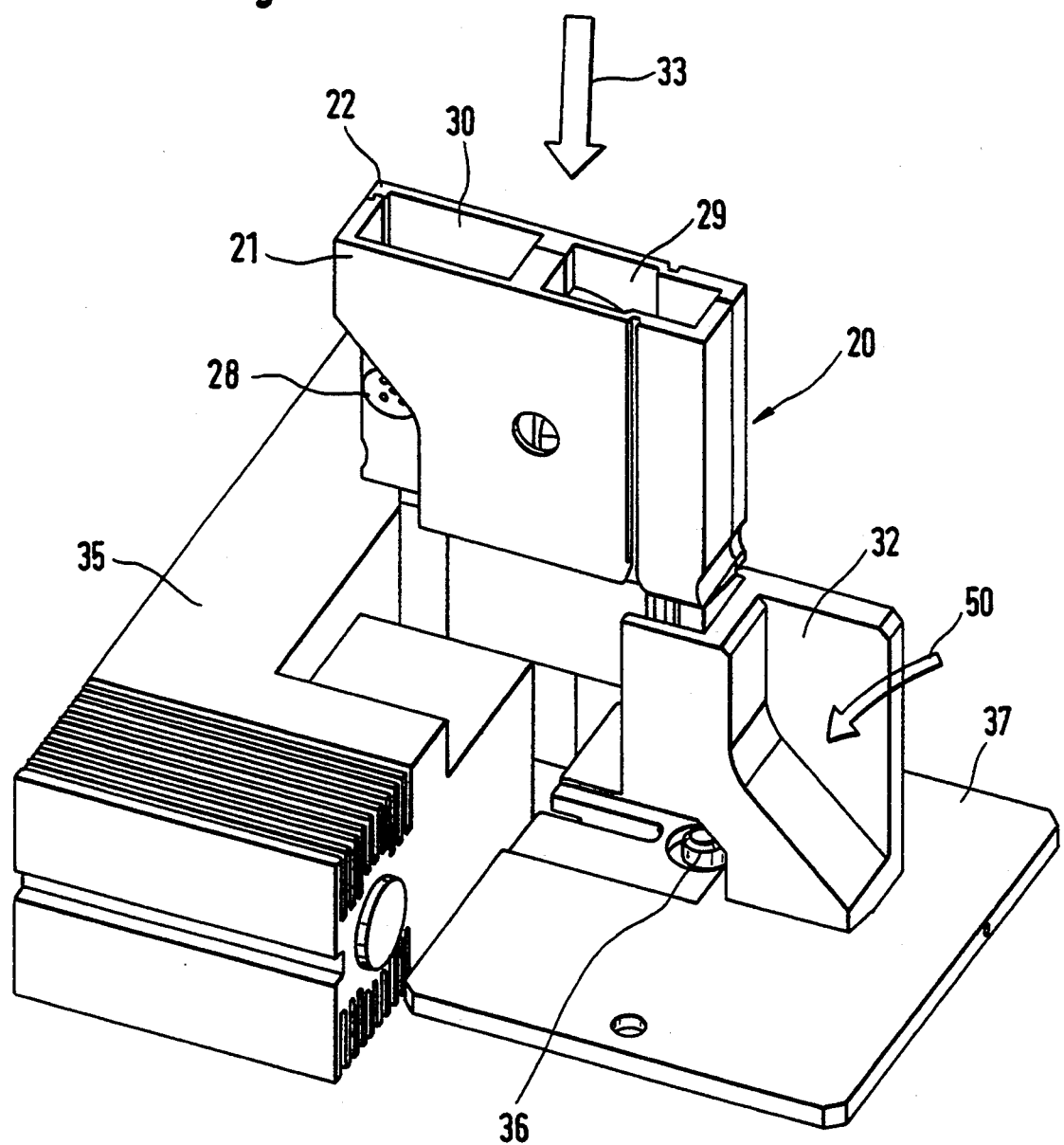
FIG. 3 depicts a part of a capillary electrophoresis apparatus of the invention in which the capillary cassette shown in FIG. 2 is inserted.

FIG. 2 depicts a capillary cassette 20 which can be inserted into a capillary electrophoresis apparatus in accordance with the invention. The cassette is shown in a perspective view with the cassette cover 21 folded upwards from the cassette base 22. When the cassette 20 is inserted into the electrophoresis apparatus, the cover 21 is folded downwards such that it lies upon the base 22. FIG. 3 shows the cassette 20 when inserted in the electrophoresis apparatus. Referring again to FIG. 2, the capillary 1 is wound as a coil around several rods 23a, 23b, etc., each of which comprises grooves for guiding the capillary 1. Due to the coiled arrangement of the capillary 1 in the cassette, a long piece of capillary tubing can be accommodated in a comparatively small volume. The ends 24 and 25 of the capillary 1 protrude from the cassette 20 as shown in FIG. 2. Near the end 25, the capillary 1 is fixed to the cassette 20 by clamping means 27. If necessary, such clamping means may also be provided at the end 24 of the capillary 1. When the cassette 20 is inserted in the electrophoresis apparatus, the ends 24 and 25 of the capillary may dip into vials, such as vials 2 and 3 shown in FIG. 1, containing electrolyte or sample liquid. The capillary 1 can easily be removed from the cassette 20 by opening the clamping means 27 and unwinding it from the rods 23a, 23b, etc.

A detector interface 28 is provided in the cassette 20 near the outlet end of the capillary 1. The outer shape of the detector interface is cylindrical. The capillary 1 is guided within the detector interface 28 and held in very precise geometrical relationship relative to the cylindrical housing of the detector interface. The detector interface 28 fits into a corresponding cylindrical recess of the detector 35 which forms part of the electrophoresis apparatus shown in FIG. 3. The detector interface is not rigidly fixed to the cassette base 22, but is arranged in a recess of the cassette base 22 which is larger than the diameter of the cylindrical housing of the interface 28. Consequently, the detector interface 28 can be shifted by a certain amount relative to the cassette base 22. Due to this floating mounting of the detector interface, a problem-free engagement of the interface with the detector is ensured. Since the capillary 1 is precisely adjusted relative to the housing of the interface and the housing precisely fits into the detector, a very good alignment of the optical system of the detector with the capillary is achieved. The cassette cover 21 comprises an opening 19 so that the detector interface 28 projects through this opening when the cassette cover 21 lies upon the cassette base 22. In that way, the detector interface 28 can communicate with the detector 35 of the electrophoresis apparatus when the cassette is inserted as shown in FIG. 3. The diameter of the opening 19 is larger than the outer diameter of the detector interface 28 so that it can move to all sides by a certain distance.

Since a considerable amount of heat can be generated during the performance of an electrophoretic separation, means for cooling the capillary are provided. The cooling is done by circulation of cooling air inside the cassette 20. For this purpose, the cassette 20 comprises an air inlet opening 29 and an air outlet opening 30 through which cooling air can enter and leave the cassette, respectively.

A locking mechanism 31 is arranged at the cassette cover 21 and a corresponding counterpart (not shown) is arranged at the cassette base 22 for firmly connecting the cover 21 with the base 22 before the cassette is inserted into the electrophoresis apparatus. The cassette 20 is made of an electrically insulating material, for example a polyurethane plastic material.

FIG. 3 depicts a part of a capillary electrophoresis apparatus of the invention in which the cassette 20 is inserted. The cassette 20 as shown in FIG. 3 is not yet completely inserted into the electrophoresis apparatus, i.e., it has not yet reached its final position at which an electrophoretic separation is performed. For reaching its final position, the cassette 20 has to be pushed somewhat further down in the direction of the arrow 33. The cassette in FIG. 3 is depicted in a position withdrawn by a distance from the final position at which electrophoresis is performed in order to show the various components of the cassette and the electrophoresis apparatus more clearly. When the cassette 20 is pushed down in the direction of the arrow 33, the detector interface 28 will engage with the mating part of the detector 35.

The cassette cover 21 and the cassette base 20 are joined together such that the cassette fits into a corresponding guidance of the cassette adapter 32 of the electrophoresis apparatus. The cassette adapter 32 is swivelling in a direction indicated by the arrow 50. The bearing for the swivelling movement is in the upper part of the electrophoresis apparatus. The purpose of the swivelling bearing of the cassette adapter is to facilitate insertion of the cassette 20 into the electrophoresis apparatus, in particular facilitating the registration of the detector interface 28 with the corresponding recess in the detector 35. For inserting the cassette 20, the operator tilts the adapter 32, pushes the cassette 20 into the guidance of the adapter, then releases the adapter so that it swings back under the action of a spring into its normal position in which electrophoresis is performed. In this normal position, the ends 24, 25 of the capillary depend vertically downwards. If the cassette adapter 32 were not swivelling, it might be difficult or even impossible to insert the cassette, since the detector interface 28 projects somewhat from the cassette 20 and could be stopped by the mating part of the detector 35 during insertion of the cassette.

At the upper portion of the cassette 20, the air inlet 29 and the air outlet 30 are provided. The electrophoresis apparatus shown in FIG. 3 comprises a high voltage insulation plate 37 to which a capillary seal and electrode arrangement 36 is fastened. The capillary seal and electrode arrangement 36 is designed for receiving the inlet end 25 (see FIG. 2) of the capillary 1. The arrangement 36 has the function to seal the capillary 1 about its periphery when it is introduced after pushing down the cassette 20 in the direction of arrow 33. The sealing function corresponds to that of the seal 9 shown in FIG. 1. Furthermore, the arrangement 36 provides an electrode (see reference numeral 5 in FIG. 1) for performing electrophoresis. It is important to note that the seal 36 in the present invention is connected to the electrophoresis apparatus and not to the cassette as in the prior art. Thus, when the cassette 20 is removed from the electrophoresis apparatus, the seal 36 remains with the electrophoresis apparatus. Furthermore, it is important to note that the arrangement 36 performs a double function in that it does not only provide for sealing of the capillary but that it also provides for the electrode function.

A further sealing and electrode arrangement with the same construction as that of the arrangement 36 is also provided in the electrophoresis apparatus for receiving the outlet end 24 of the capillary 1. The provision of a seal at the outlet end has the purpose to enable injection of liquids into the capillary by application of sub-atmospheric pressure at the outlet end. If, however, this possibility is not required, the seal at the inlet end would not be necessary. The electrode is of course required in any case.

Figure 4:
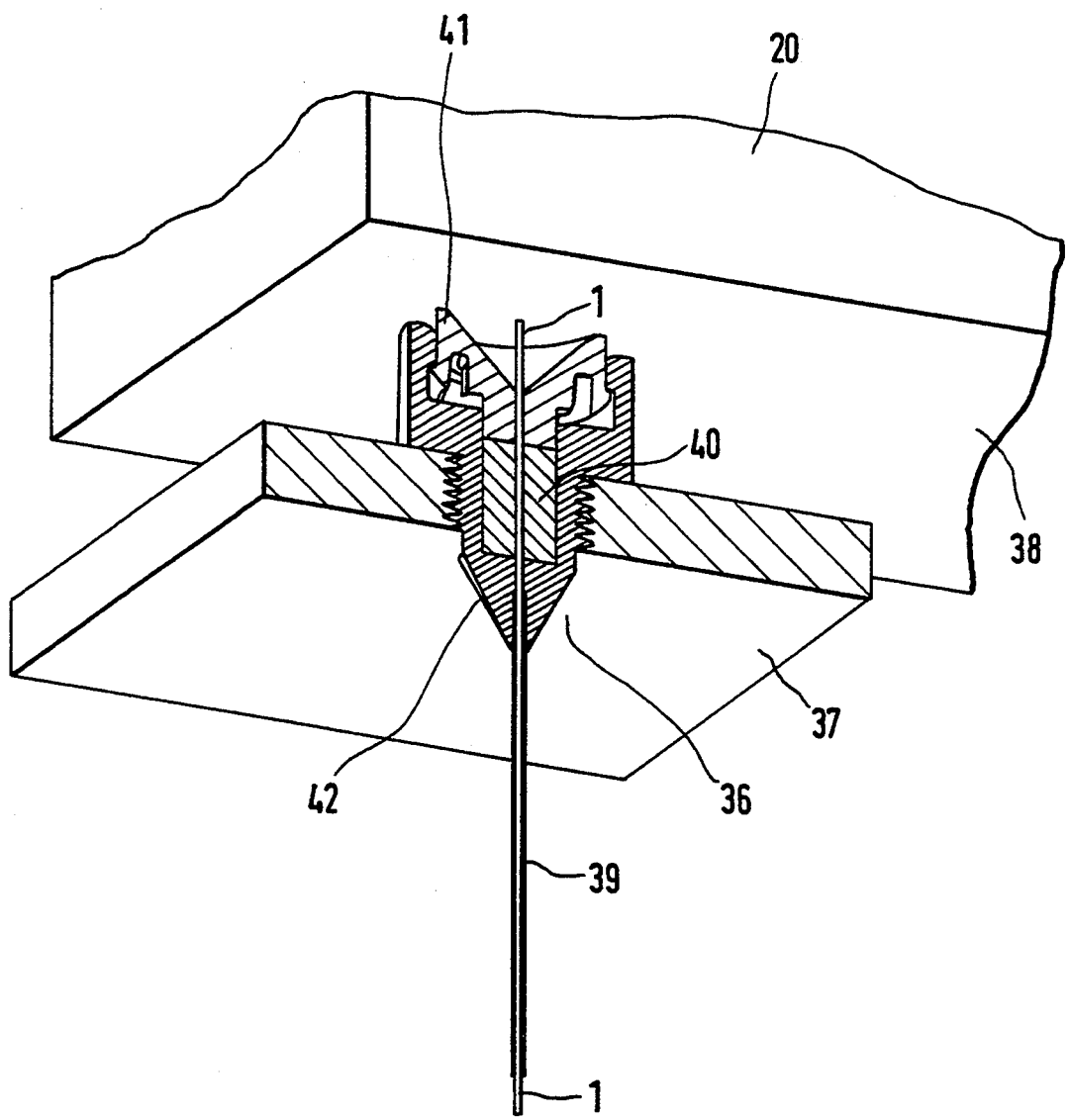
FIG. 4 shows a cross section through a part of the apparatus shown in FIG. 3 comprising the sealing and electrode arrangement according to the invention.

In the following, the seating and electrode arrangement will be described in more detail with reference to FIGS. 4 and 5. FIG. 4 shows a cross section through a part of the apparatus shown in FIG. 3 comprising the sealing and electrode arrangement 36. The sealing and electrode arrangement 36 is fixed to the high voltage insulation plate 37. For fixing the arrangement 36, it may comprise, for example, a thread at its outer surface by which it is screwed into the insulation plate 37. The arrangement 36 comprises a tube 39 of electrically conductive material which serves as an electrode. The inner diameter of the electrode tube 39 is selected such that the capillary 1 can be pushed through it.

FIG. 4 corresponds to the situation that the cassette 20 is inserted in the electrophoresis apparatus. The capillary 1 projects from the bottom 38 of the cassette 20 and extends along the center axis of the arrangement 36 and through the electrode tube 39. The sealing function is accomplished by means of a silicone rubber seal 40. The electrode and sealing arrangement 36 also comprises a funnel 41 which has the purpose to capture the capillary 1 when the cassette 20 with the projecting end 25 of the capillary 1 is moved downwards (along arrow 33 in FIG. 3) during insertion of the cassette into the electrophoresis apparatus.

Figure 5:
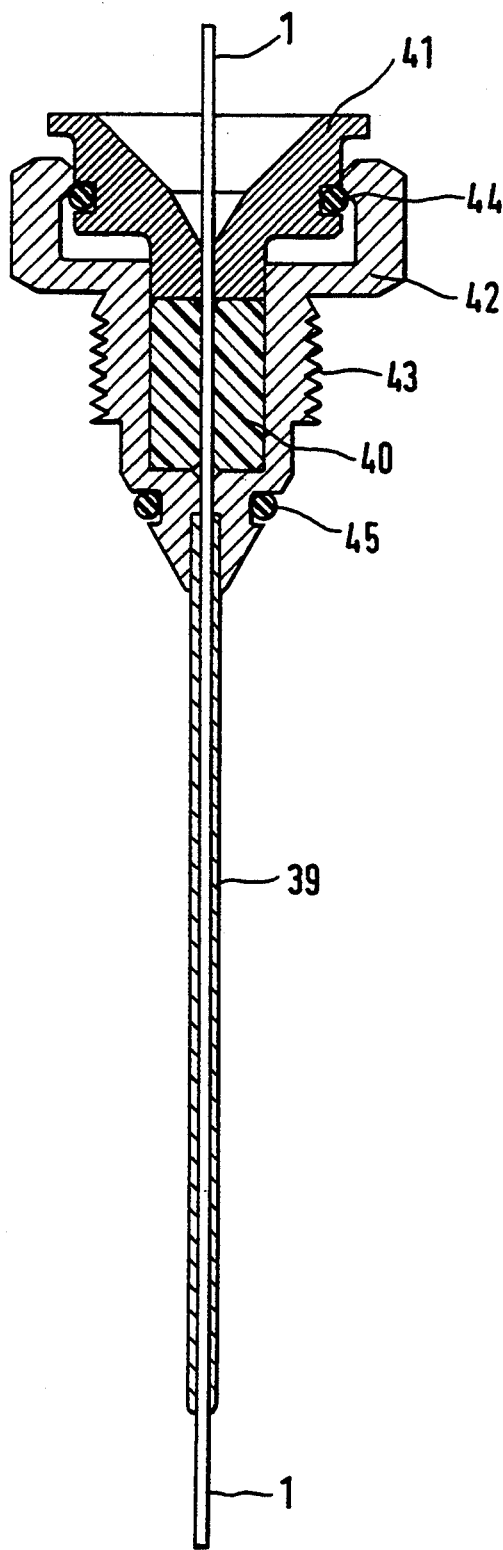
FIG. 5 is a detailed cross sectional view of the sealing and electrode arrangement according to FIG. 4.

FIG. 5 depicts the sealing and electrode arrangement 36 in more detail. The housing 42 accommodates the seal 40 and the funnel-shaped part 41 and holds the electrode tube 39. The housing is made of an electrically conductive material. The outer surface of the housing comprises a threaded portion 43 which can be screwed into the insulation plate 37 of the electrophoresis apparatus. The electrode tube 39 is pressed into the housing 42. A typical material for the electrode tube is platinum. The funnel-shaped part 41 is held in place in the housing by means of an O-ring 44. In an embodiment of the invention, the part 41 is made of a plastic material. A second O-ring 45 is arranged at the lower part of the housing. The function of the O-ring 45 will be explained below in connection with FIG. 6.

When inserting the cassette 20 into the electrophoresis apparatus, the end 25 of the capillary 1 is caught by the funnel 41 and guided through the seal 40 and the electrode tube 39. The electrophoresis apparatus of the invention comprises a door (not shown) which has to be closed before the operation of the apparatus can start. Associated with this door is a resilient element which exerts a force on the cassette 20 in the direction indicated by the arrow 33 (FIG. 3) when the door is closed. This force urges the bottom 38 of the cassette 20 against the upper edge of the funnel-shaped part 41. The part 41 thus deforms the elastomeric seal 40 so that it contacts the capillary 1 and the housing 42 and forms a tight seal. When the door of the electrophoresis apparatus is opened again, the elastomeric seal 40 can relax and thus releases the capillary which had been squeezed in by the seal 40. In an embodiment of the invention, the force by which the cassette 20 is pressed against the funnel 41 is about 50N. The sealing of the capillary is thus performed automatically when the door of the electrophoresis apparatus is closed; the operator does therefore not have to take care of the sealing of the capillary.

When the cassette 20 has been pushed into its final position in the electrophoresis apparatus, the end of the capillary 1 projects beyond the lower end of the tube electrode 39. In an embodiment of the invention, the capillary projects from the lower end of the electrode by about 5 mm. During an electrophoretic separation, a high voltage is applied via the electrode 39 which dips into an electrolyte vial. The high voltage is supplied to the electrode 39 by means of a conductive annular eyelet which is jammed between the housing 42 and the insulation plate 37 of the electrophoresis apparatus.

Figure 6:
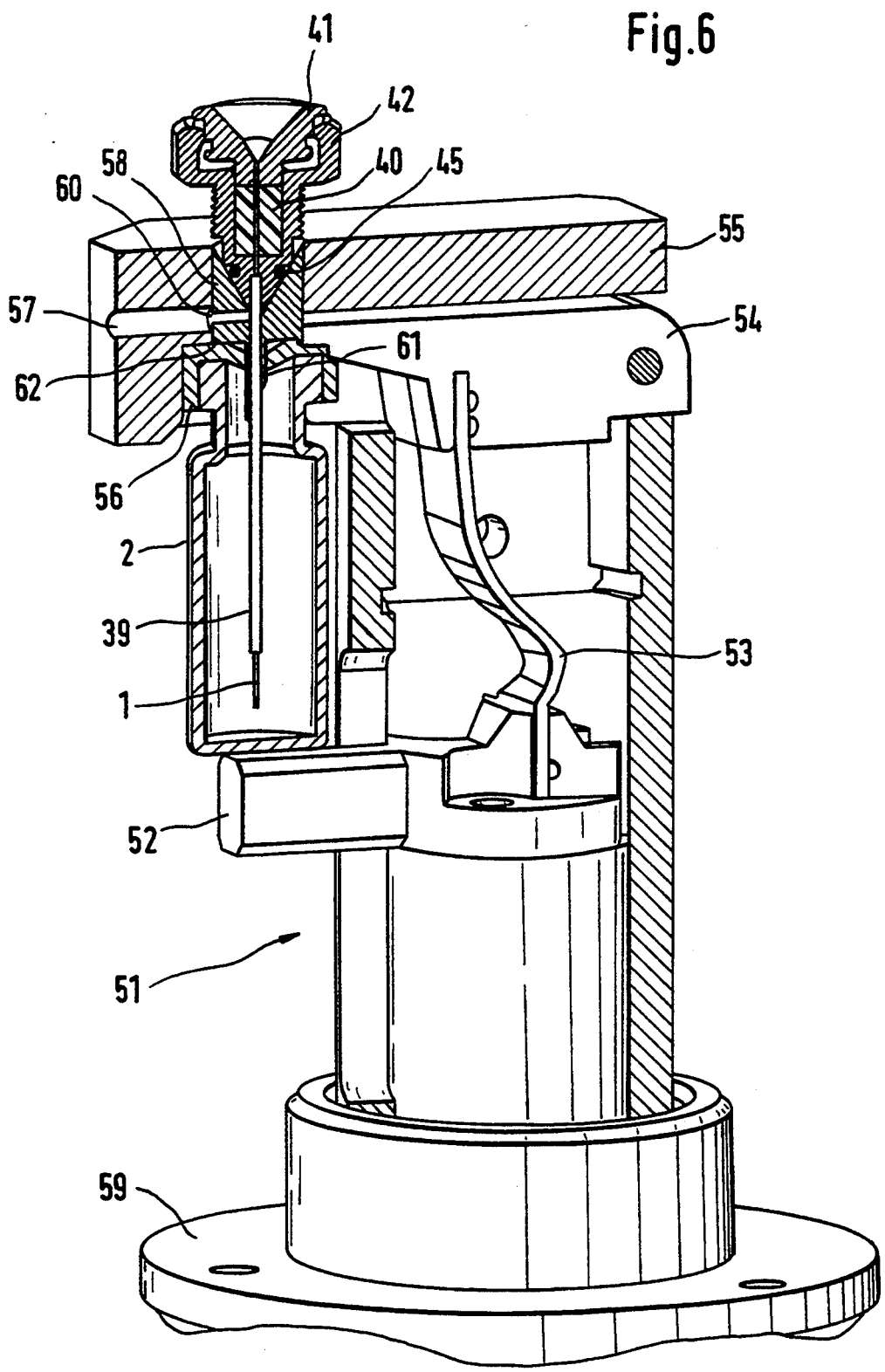
FIG. 6 shows a cross section through a part of the electrophoresis apparatus comprising a lifting mechanism for lifting a vial to the sealing and electrode arrangement according to FIGS. 4 and 5.

In the following, it will be described in more detail with reference to FIG. 6 how a vial containing sample or electrolyte is positioned at the sealing and electrode arrangement described above. Furthermore, it will be described, how pressure is introduced into a vial for forcing liquid into the capillary. FIG. 6 shows a cross section through a part of the electrophoresis apparatus of the invention comprising a lifting device 51 for lifting or lowering a vial 2, and further comprising the sealing and electrode arrangement with the housing 42, the elastomeric seal 40, the funnel 41, and the tubular electrode 39. As shown in FIG. 4, the housing 42 is fixed by means of a thread 43 to an insulation plate 37. In FIG. 6, however, the insulation plate 37 was omitted so that the remaining parts of the apparatus can be seen more clearly.

The lifting device 51 shown in FIG. 6 is mounted to a platform 59 which is a part of the electrophoresis apparatus. The lifting device 51 is movable in a vertical direction such as to move the vial 2 towards the sealing and electrode arrangement. The lifting device 51 comprises a head portion 55 wherein a funnel shaped member 58 is inserted which can accommodate the corresponding cone shaped lower part of the housing 42 when the head portion 55 is moved upwards. The head portion 55 has a recess into which the top of the vial 2 fits. The bottom of the vial 2 is held by a finger 52 which is also movable in a vertical direction. The finger 52 is used for lifting the vial 2 out of a vial tray (not shown) and pressing it into the mentioned recess of the head portion 55. After the top of the vial 2 has been pressed into this recess, the entire lifting device including the finger 52 and the head portion 55 are moved upwards until the funnel shaped member 58 is in contact with the cone of the housing 42 as shown in FIG. 6. The vial 2 is closed with a septum 56 which has been pierced by a punching needle 61 which protrudes downwards from the member 58. The member 58 also comprises an annular cutting edge 62 surrounding the punching needle 61. The cutting edge 62 cuts into the septum 56 when the vial 2 is pressed against the head portion 55 and thus provides for a sealing of the member 58 against the vial 2. When the vial 2 is to be positioned back in the vial tray, the lifting device 51 and the finger 52 have to be lowered. In order to ensure that the vial is removed again from the punching needle when it is lowered, a rocking lever 54 and an actuation belt 53 are provided. When the finger 52 has been moved sufficiently far downwards, the actuation belt 53 is tightened, causing a tilting of the rocking lever whereby the vial 2 is stripped off the punching needle 61. Further details of the lifting device and the vial tray are contained in a European patent application entitled "Apparatus for Handling Liquid Vials in an Analytical Device", filed by applicant of the present European patent application on the same date as the present application (U.S. application No. 08/086,589 filed Jul. 1, 1993).

Referring again to FIG. 6, it will now be described how pressure is applied to the liquid in the vial 2 for forcing liquid into the capillary 1. The pressure is applied through a pressure inlet channel 57 which is arranged in the head portion 55 and through a channel 60 in the member 58 communicating with the channel 57. A suitable source of overpressure (not shown) is connected to the channel 57. The pressure is transmitted through the channels 57 and 60 and the interior of the punching needle 61 into the vial 2, forcing liquid from the vial into the capillary 1. In order to prevent escaping of the pressure, various seals are provided: First, the bottom of the member 58 has the mentioned cutting edge 62 which cuts into the septum 56 and seals there. Second, an O-ring 45 at the sealing and electrode arrangement (see also FIG. 5) is provided to prevent escaping of pressure through the funnel of the member 58. Finally, the seal 40, provides a seal around the capillary 1.

According to a practical embodiment of the invention, the electrode 39 has an inner diameter of 0.5 mm, an outer diameter of 1 mm and a length of 44 mm. The capillary 1 has an outer diameter of 0.4 mm. The punching needle 61 has an inner diameter of 1.4 mm and an outer diameter of 2 mm. The silicone rubber seal 40 has an outer diameter of 4 mm and a length of 6 mm. The central bore in the seal 40 has a diameter of 0.5 mm. The funnel 41 has a diameter of 8 mm at its upper end and is made of a plastic material which is chemically resistant and has low friction with the capillary 1. The compression travel of the funnel 41 when a force is applied on it deforming the seal 40 is about 0.2 to 0.3 mm.

In the above described embodiment of the invention, the electrode 39 surrounds the capillary 1. This arrangement has several advantages, some of which are mentioned above. Another advantage of this arrangement is that the electrode tube 39 protects the capillary against any damages. It is understood, however, that alternative designs for the electrode would be possible. For example, the electrode could be a conductive rod which extends in parallel to the capillary into a vial containing electrolyte and/or sample, similar to the arrangement schematically depicted in FIG. 1.

According to the embodiment shown in FIGS. 2 to 6, the high voltage is supplied to the electrode 39 by means of a conductor which is fastened to the housing 42 accommodating the elastomeric seal 40. In an alternative embodiment of the invention, the connection to high voltage could be provided in the lifting device 51 for lifting the vial 2.

According to a further alternative embodiment of the invention, the seal around the end of the capillary 40 could be designed as two elastomeric jaws which are pressed together for providing a seal around the periphery of the capillary. Other embodiments of the seal would also be possible within the concept of the present invention; it is only essential that the seal around the periphery of the capillary is associated with the electrophoresis apparatus. It is also understood that the fastening of the sealing and electrode arrangement to the electrophoresis apparatus could be different from the embodiment shown in FIG. 4.

In the embodiment described above in connection with FIGS. 2 to 5, the sealing arrangement is rigidly connected to the electrophoresis apparatus, whereas the cassette 20 is still movable by a small distance after it has been inserted into the electrophoresis apparatus. As explained above, the bottom of the cassette exerts a force on the seal 40 via the funnel 41, while the cassette travels this small distance to its end position in the electrophoresis apparatus. As an alternative to this design, it is also possible to mount the sealing arrangement in a floating manner so that it is movable by a small distance in a direction along the longitudinal axis of the projecting capillary end and to keep the cassette in a fixed position. In this embodiment, the force for deforming the elastomeric seal would have to be provided from the opposite direction as in the embodiment of FIGS. 2 to 5, i.e., from below. This force could be provided, for example, by a mechanism connected to the door of the electrophoresis apparatus so that the seal is deformed when the door is closed, or it could be provided by a separate means, e.g. a lever to be activated by the operator.

I claim:

1. An apparatus for performing capillary electrophoresis, comprising:
   a removable cassette including a capillary, the capillary having an inlet end and an outlet end, with the inlet end and the outlet end projecting from the cassette,
   a housing for receiving the cassette to enable electrophoresis action through said capillary,
   said housing including a sealing arrangement for forming a seal around an end of the capillary when the cassette is inserted in the housing, said housing further including positioning means for enabling said cassette to cause engagement between said end of the capillary and said sealing arrangement, said sealing arrangement actuated to provide a seal between said end of the capillary and said housing when said cassette is in a final position of said engagement.

2. An apparatus as in claim 1, wherein the sealing arrangement comprises an elastomeric seal, and wherein the sealing effect is achieved by a deformation of the seal by application of a force on the seal.

3. An apparatus as in claim 1, comprising a funnel-shaped part associated with the sealing arrangement for capturing an end of the capillary when the cassette is inserted into the housing of the electrophoresis apparatus.

4. An apparatus as in claim 3, wherein the funnel-shaped part is resiliently mounted by elastic means such that the funnel-shaped part is pressed against the seal when a force is applied on it via a bottom of the cassette, thereby causing a deformation of the seal, resulting in the sealing off of the capillary.

5. An apparatus as in claim 1, further comprising a tube-shaped electrode connected to the sealing arrangement, with the capillary passing through an interior lumen of the tube-shaped electrode when the cassette is inserted into the housing of the electrophoresis apparatus.

6. An apparatus as in claim 1, wherein the cassette comprises a housing and a detector interface which is movable relative to the housing of the cassette, with an outlet end of the capillary being guided through the detector interface.

7. An apparatus as in claim 1 further comprising a swiveling cassette adapter for insertion of the cassette into the electrophoresis apparatus.

8. An apparatus as in claim 1, further comprising a lifting device for lifting a vial containing electrolyte or sample liquid such than an electrode for performing electrophoresis and the capillary are immersed in the liquid in the vial with the lifting device comprising a head portion which is sealed against an elastomeric seal within the housing accommodating the elastomeric seal by sealing means when the head portion is pressed against the housing.

9. An apparatus as in claim 8, wherein the head portion of the lifting device comprises a cutting edge which cuts into a septum of the vial in a sealing manner when the vial is pressed against the head portion.

10. An apparatus as in claim 8, wherein the head portion of the lifting device comprises a punching needle for punching a hole into the septum of the vial, the interior of the punching needle providing a passage for the electrode and the capillary.

11. An apparatus as in claim 10, wherein the head portion comprises a channel through which pressure can be supplied to the vial.

12. The apparatus as recited in claim 1 wherein actuation of said sealing arrangement occurs as a result of contact between said cassette and said sealing arrangement and occurs when said cassette moves into a final position of said engagement.

* * * * *